(12) United States Patent
Stelmach

(10) Patent No.: US 8,114,038 B2
(45) Date of Patent: Feb. 14, 2012

(54) ORAL HYGIENE APPARATUS

(76) Inventor: John Stelmach, Prescott, AZ (US)

( * ) Notice: Subject to any disclaimer, the term of this patent is extended or adjusted under 35 U.S.C. 154(b) by 974 days.

(21) Appl. No.: 12/103,279

(22) Filed: Apr. 15, 2008

(65) Prior Publication Data
US 2009/0259153 A1    Oct. 15, 2009

(51) Int. Cl.
*A61H 13/00* (2006.01)
(52) U.S. Cl. .................. 601/165; 601/160; 601/162
(58) Field of Classification Search .............. 601/161, 601/162, 163, 164, 165, 169; 433/80, 82, 433/87, 140; 401/42, 289
See application file for complete search history.

(56) References Cited

U.S. PATENT DOCUMENTS

| | | | |
|---|---|---|---|
| 4,650,470 A | | 3/1987 | Epstein |
| 5,027,798 A | * | 7/1991 | Primiano ............... 601/165 |
| 5,095,893 A | | 3/1992 | Rawden |
| 5,385,533 A | | 1/1995 | Coviello |
| 5,685,851 A | * | 11/1997 | Murphy et al. ......... 604/150 |
| 6,056,710 A | | 5/2000 | Bachman |
| 6,740,053 B2 | | 5/2004 | Kaplowitz |
| 6,835,181 B2 | | 12/2004 | Hippensteel |
| 2007/0203439 A1 | * | 8/2007 | Boyd et al. ............. 601/162 |
| 2007/0261163 A1 | | 11/2007 | Lynam |

OTHER PUBLICATIONS 1 sheet from a website, showing a Waterpik Ultra Cordless Dental Water Jet WP-450.

* cited by examiner

*Primary Examiner* — Quang D Thanh
(74) *Attorney, Agent, or Firm* — Sturm & Fix LLP

(57) ABSTRACT

A method and apparatus for oral hygiene, in particular having an oral hygiene device similar to a WATER PIK® brand device which has a pump with an inlet port and an outlet nozzle. A reservoir is placed in a sink above a drain and below a faucet and water from the faucet is adjusted for temperature and flows into the reservoir and over and into the drain of the sink. A conduit is provided between the inlet of the pump and the outlet of the reservoir so that, in use, a person can first adjust the temperature of the water in the reservoir and then turn on the pump and use the oral hygiene device as with any other oral hygiene apparatus while either allowing the water to continue to flow from the faucet at the desired temperature; or, if desired, to stop the flow and put medication into the container before use so that the water and medication solution is used rather than just water.

15 Claims, 7 Drawing Sheets

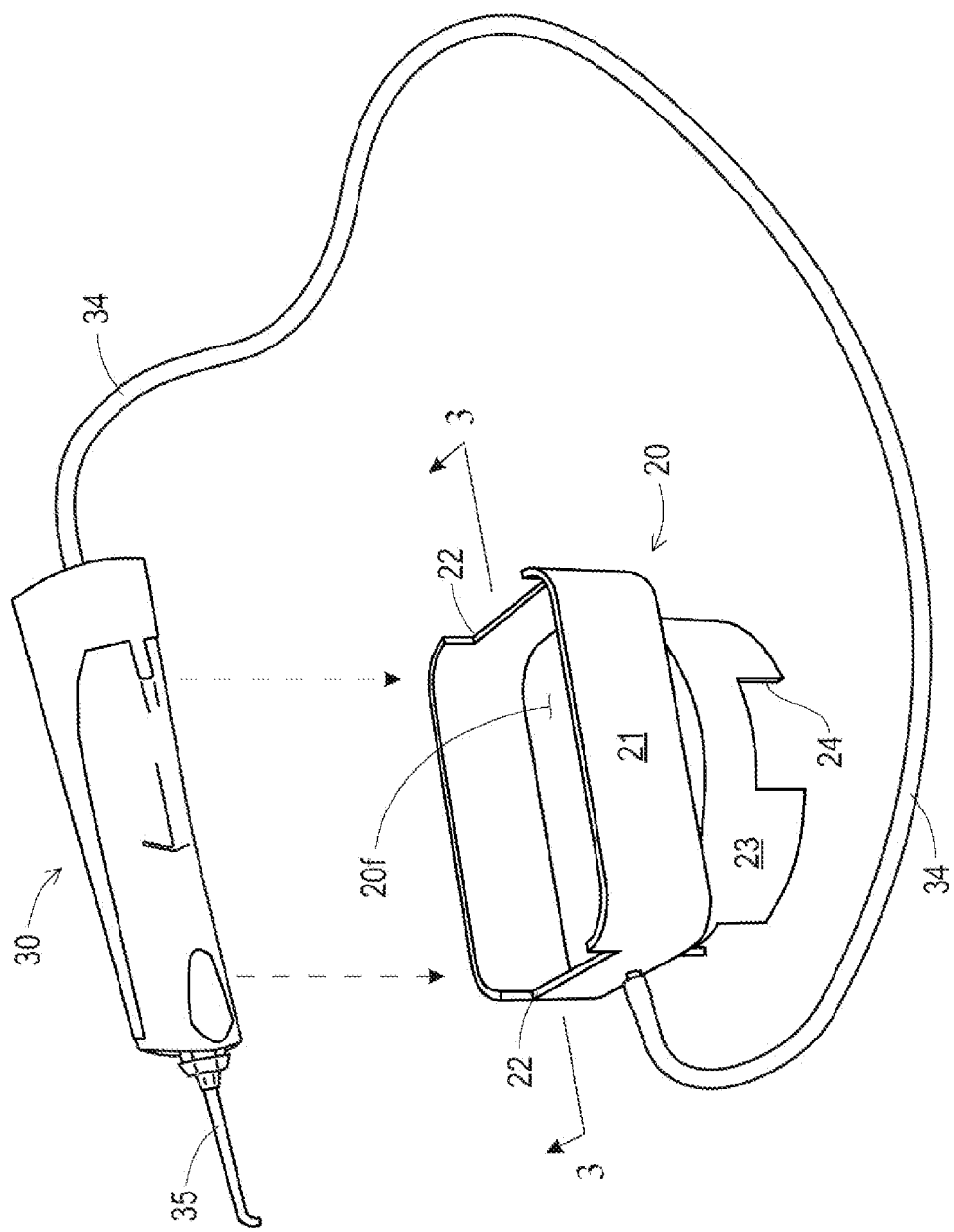
Fig. 2-a

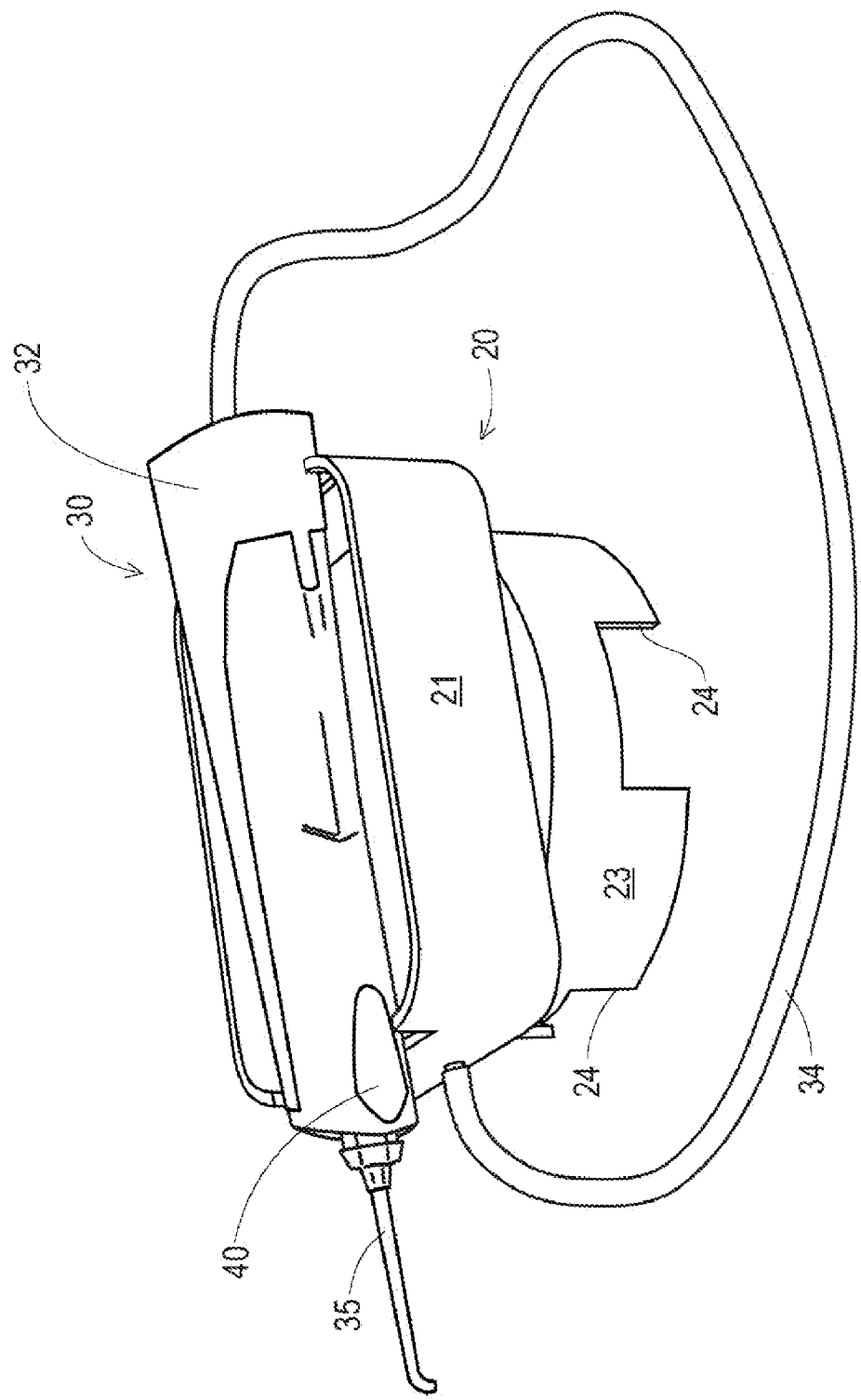
Fig. 2-b

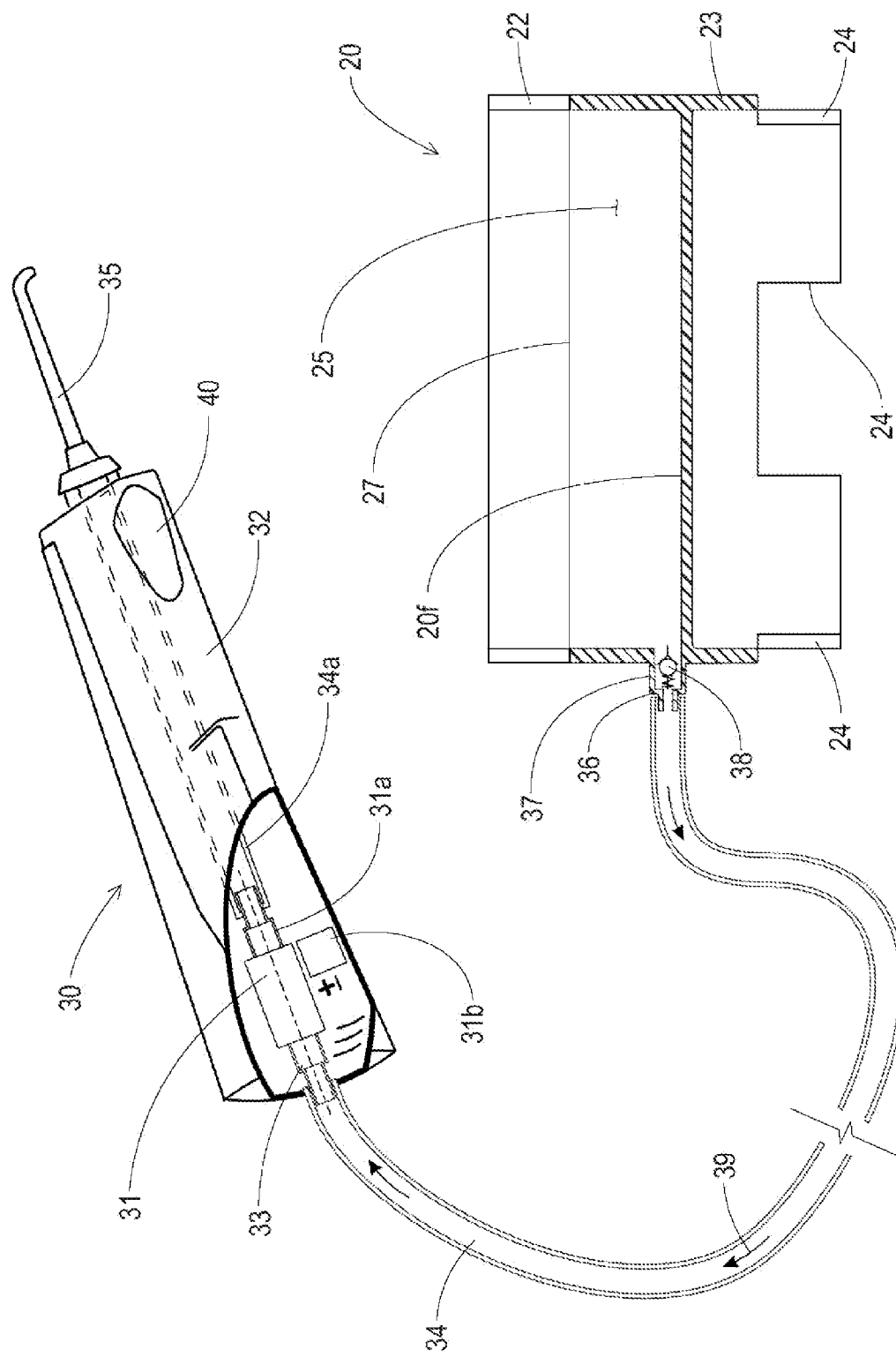

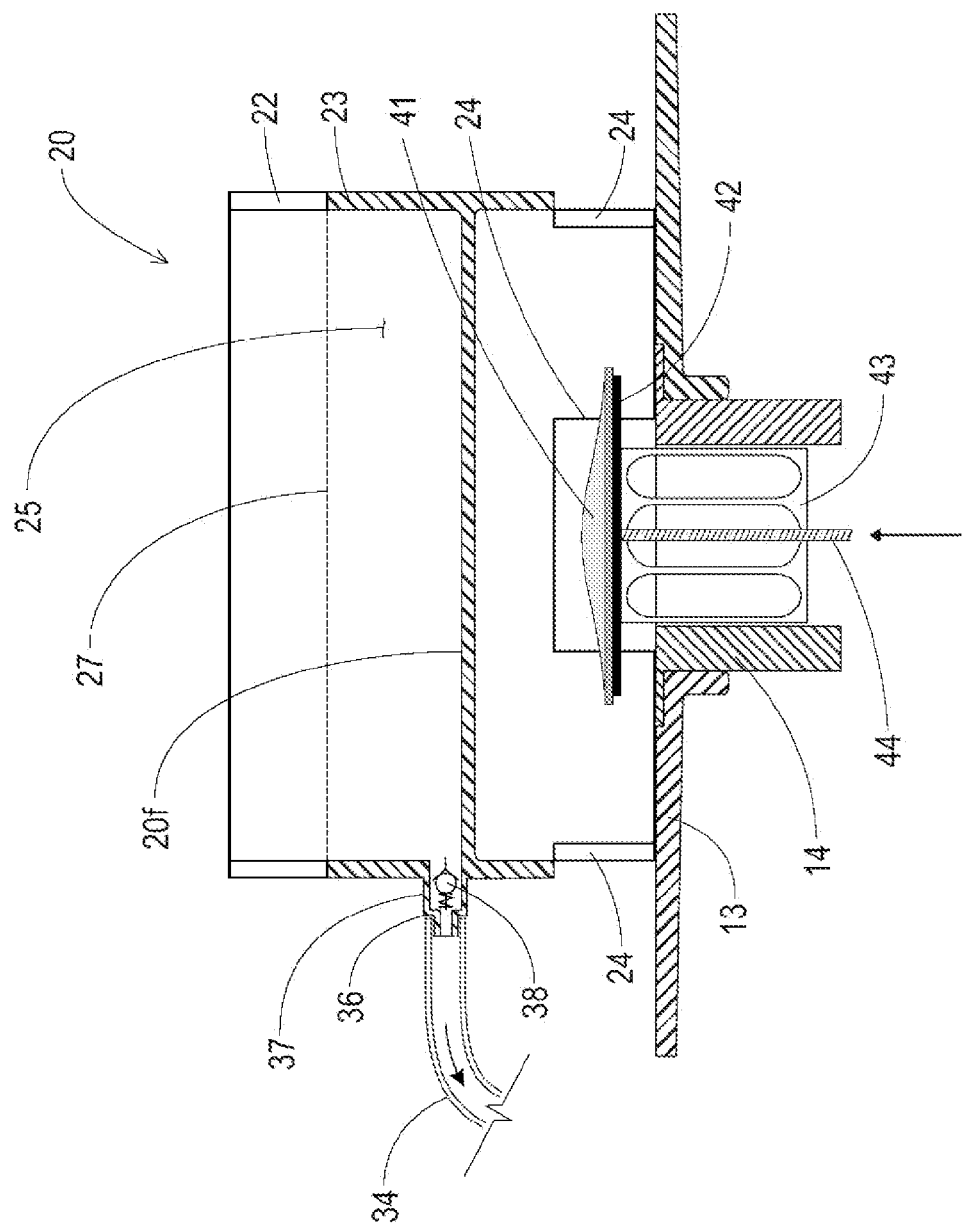
Fig. 5-a

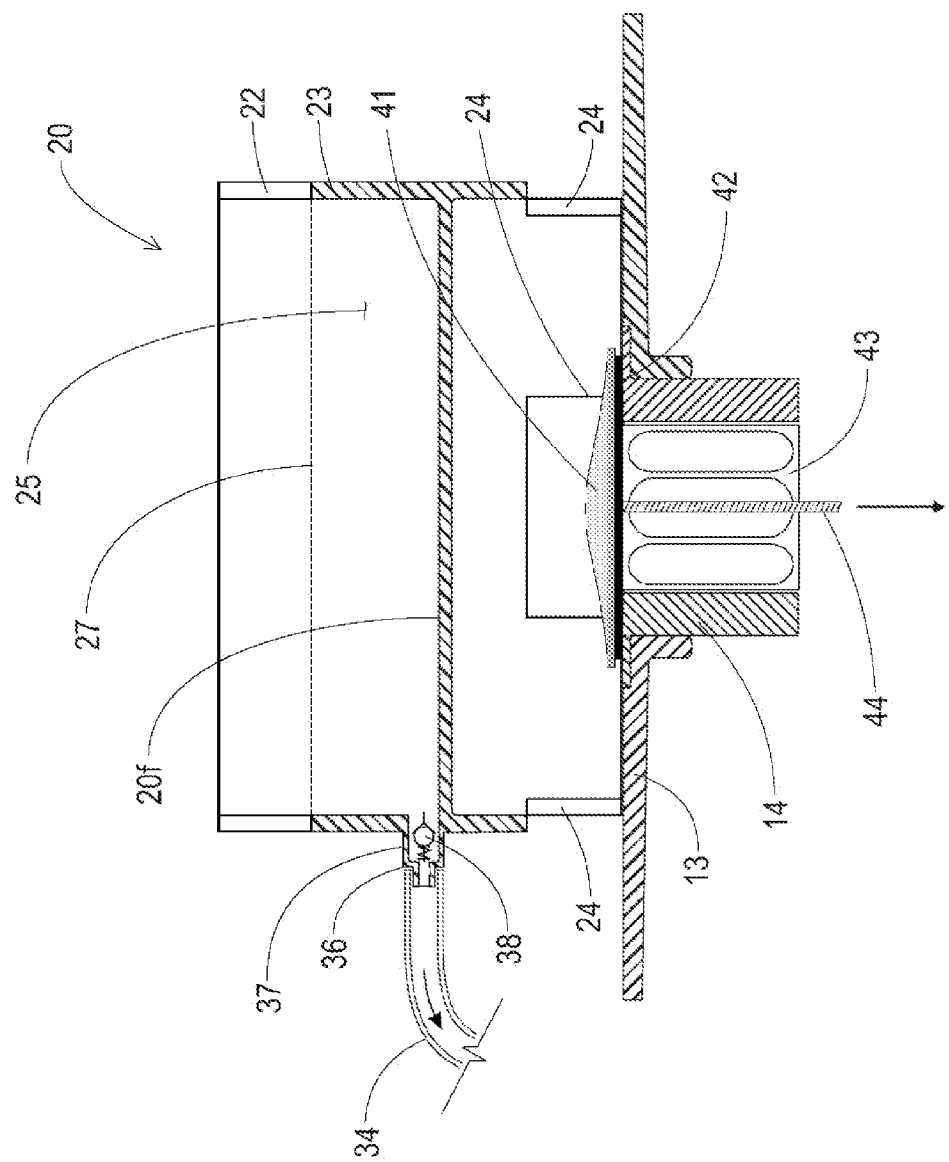
Fig. 5-b

ORAL HYGIENE APPARATUS

CROSS-REFERENCE TO RELATED APPLICATIONS

Not Applicable

BACKGROUND OF THE INVENTION

Field of the Invention

The present invention relates generally to an oral hygiene apparatus of a type that has a nozzle and a pump for providing pressurized water to a person's teeth and gums for oral hygiene purposes. One such device is a WATER PIK® brand, Ultra Cordless Dental Water Jet WP450. One of the problems with this device is that it has a self-contained reservoir for receiving and holding water which is detachable and becomes part of the handle itself. Typically there is not enough capacity in this reservoir to provide all of the water needed for a complete use of this device in cleaning a person's gums and teeth.

Improvements have been made to the WATER PIK® device just described wherein a connection is made to the water faucet so that water can flow directly from the water faucet to the oral hygiene device itself, sometimes with an intermediate accumulating container for holding water. One of these devices is shown in U.S. Pat. No. 6,740,053 to Kaplowitz, which patent is incorporated herein by reference. Another such device is shown in U.S. Pat. No. 6,853,181 to Hippensteel, which is also incorporated herein by reference and which has an intermediate accumulating container. U.S. Pat. No. 5,385,533 to Coviello, which is also incorporated herein by reference, is similar to the Kaplowitz device in that it does not have an intermediate accumulating container.

In Coviello and Kaplowitz, devices that connect directly to a faucet, it is difficult to put medication into the water. U.S. Pat. No. 6,057,710 to Bachman, which is also incorporated herein by reference, shows a container for holding water when the device is in use and which container can be flipped over to facilitate storage when not in use. A particular problem with the Bachman device is water temperature adjustment. It would not be a good idea to put the entire Bachman device into a sink and let the water run into the reservoir until it overflows while the water temperature is adjusted to a desired temperature because the working parts of the oral hygiene device can be damaged if they become wet. The Bachman reservoir alone cannot be deployed in a sink during use of the high pressure nozzle because it needs to be attached to the pump housing during use of the pump and nozzle, so the water temperature in the Bachman container cannot be regulated as easily as might be desired.

Accordingly there is a need for an oral hygiene apparatus which overcomes the shortcomings of the prior art discussed above.

BRIEF SUMMARY OF THE INVENTION

The present invention relates generally to a method and apparatus for oral hygiene, in particular the invention relates to a device having an oral hygiene device similar to a WATER PIK® brand device which has a pump with an inlet port and an outlet nozzle. A reservoir is placed in a sink above a drain and below a faucet and water from the faucet is adjusted for temperature and flows into the reservoir and over and into the drain of the sink. A conduit is provided between the inlet of the pump and the outlet of the reservoir so that, in use, a person can first adjust the temperature of the water in the reservoir and then turn on the pump and use the oral hygiene device as with any other oral hygiene apparatus while either allowing the water to continue to flow from the faucet at the desired temperature; or, if desired, to stop the flow and put medication into the container before use so that the water and medication solution is used rather than just water.

An object of the present invention is to provide a method and apparatus to facilitate easy adjustment of the water temperature while using an oral hygiene device.

Another object of the present invention is to provide an oral hygiene apparatus which has a virtual unlimited supply of water.

A further object of the invention is to provide an oral hygiene apparatus which facilitates easy introduction of medication into the water being used; and A reservoir which can be easily cleaned and serves as a compact holder for the WATER PIK® type device when not in use. Other objects, advantages, and novel features of the present invention will become apparent from the following detailed description of the invention when considered in conjunction with the accompanying drawings.

BRIEF DESCRIPTION OF THE DRAWINGS

FIG. 2-a is an enlarged perspective view of the oral hygiene apparatus of the present invention shown in readiness to be placed in a storage position after use;

FIG. 2-b is an enlarged perspective view of the oral hygiene apparatus of the present invention, not in the sink, shown in a storage position;

FIG. 3 is a partial cross sectional view of the present invention showing the reservoir with a slotted base and a housing for being held in a user's hand, which housing has a pump therein having an inlet connected by a conduit to the outlet of the reservoir and the outlet of the pump extending to the outlet nozzle on the housing;

FIG. 5-a is a cross sectional view like FIG. 3 but showing a stopper of a drain in the "up" or drainage position thereof; and FIG. 5-b is a cross sectional view like FIG. 5-a but showing a stopper of a drain in the "down" or closed position thereof.

DESCRIPTION OF THE PREFERRED EMBODIMENT

Figure 1:
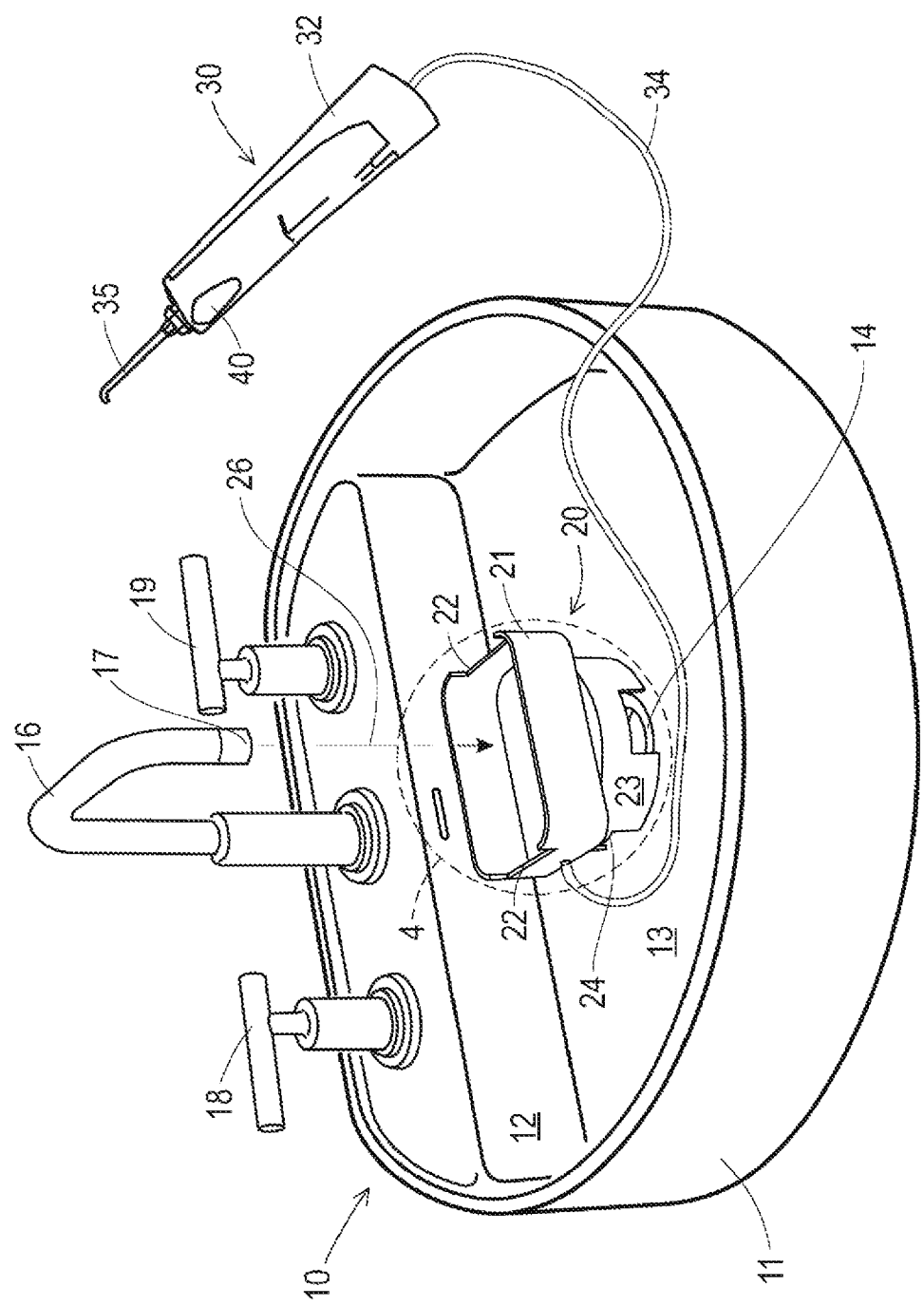
FIG. 1 is a perspective view of the present invention showing a sink with a hot and cold water supply and a drain and having the reservoir of the present invention disposed over the drain and such water supply being connected with a conduit to a pump and nozzle enclosed in a housing.

Referring now to the drawings wherein like reference numerals designate identical or corresponding parts throughout the several views, FIG. 1 shows an oral hygiene apparatus 10 constructed in accordance with the present invention. A sink 11 has a basin 12 with a lower wall 13 having a drain 14 disposed therein. The sink 11 also has a faucet 16 with an outlet opening 17 therein. As with most sinks, it has a hot water valve 18 on the left and a cold water valve 19 on the right, but of course these could be reversed. A reservoir 20 has an upper portion with a wall 21 that goes completely around the container a floor 20f and the ends of this wall 21 have slots 22 disposed therein for reasons which will be explained below.

A base 23 of the container has four openings or slots 24 formed in the bottom thereof the purpose of which will be explained below in the operation of the device. The arrow 26 indicates that the water from the faucet 16 will flow downwardly by gravity into the container 20 and it is noted that the base 23 is placed directly over the drain 14 of the sink 11 during use primarily so the reservoir can be directly beneath the faucet outlet opening 17.

Referring now to FIG. 3, the container 20 having the slots 22 therein permits water from the outlet 17 of the faucet 16 to flow into portion 25 below the dashed line 27. Clearly once the water reaches the level 27 it will flow out of the container 20 through the slots 22 and into the bottom 13 of the sink 11. Then the water will flow downwardly through lower openings 24 in the base 23 and out the drain 14 shown in FIG. 1.

Figure 4:
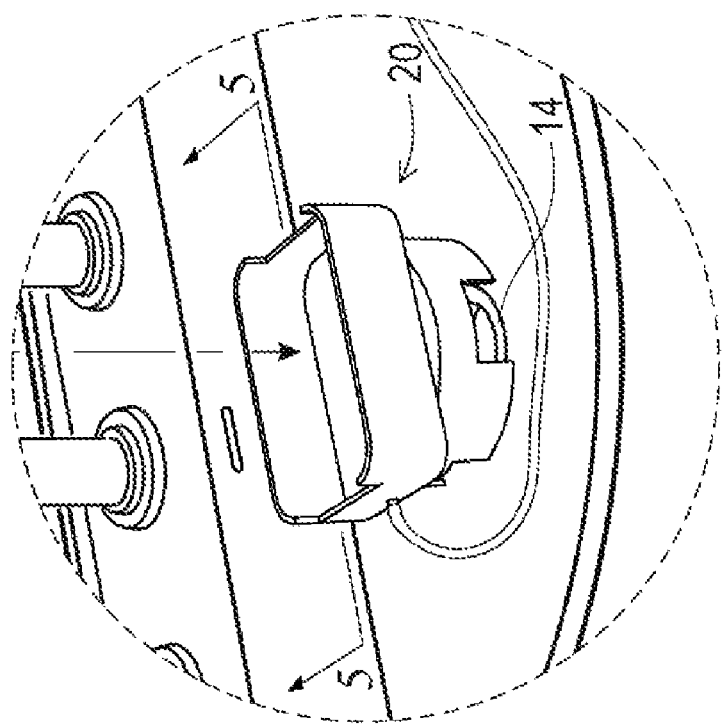
FIG. 4 is an enlarged perspective view of the oral hygiene apparatus of the present invention shown inside the dashed line circle 4 of FIG. 1.

Referring to FIGS. 4, 5-*a* and 5-*b* a drain 14 is disposed in the bottom 13 of the sink 11. A stopper 41 is positioned in the opening of drain 14 and is moveable between the open position shown in FIG. 5-*a* and the closed position in FIG. 5-*b*. An actuator 44 of a conventional type which can be accessible from the top of the sink 11, can be used to move the stopper 41 between the open and closed positions shown in FIGS. 5-*a* and 5-*b*. It is important that there be adequate clearance between the floor 20*f* of the reservoir 20 and the stopper 41 in the open position shown in FIG. 5-*a*.

A rubber seal 42 attached to the bottom of stopper 41 seals between the drain 14 and the stopper 41 as shown in FIG. 5-*b*. A strainer 43 is attached to the bottom of the stopper 41 which keeps the stopper 41 aligned in the opening of the drain 14 as it moves between the open and closed positions of FIGS. 5-*a* and 5-*b*.

Connected to the reservoir 20 is an oral hygiene device 30 which can be like the WATER PIK® Model WP450 which has a pump 31 inside a housing 32. A pump 31 can be operated by a battery source 31*a* or can be plugged into house current at 31*a* depending upon whether a battery operated device is desired or not.

The inlet 33 of the pump 31 has a flexible conduit 34 attached thereto and the other end of the conduit 34 is attached to a fitting 36 at the outlet 37 of the reservoir 20. A one-way check valve 38 is disposed in the outlet 37 to allow flow only in the direction of the arrows 39 in the conduit 34 so that water cannot flow back into the reservoir 20. This also keeps the pump 31 primed with water at all times. This check valve 38 could alternatively be located at the inlet port 33 of the device 30 instead of the way it is shown in FIG. 3, or for that matter anywhere in the line of the conduit 34. The pump 31 has an outlet 31*a* connected to another conduit 34*a* which leads to a nozzle 35.

In operation of the present invention, the container 20 is placed in the position shown in FIG. 1 and the hot and cold faucets 18 and 19 are opened until water passing down into the container 20 is at a proper temperature which typically can be determined if the user just puts their hand or finger in the reservoir 20 and feels the flow as it passes from the faucet 16 to the reservoir 20. Slots 22 allow the excess water to pass to the drain 14 instead of accumulating in the bottom of the sink 11 and perhaps even causing the reservoir 20 to move or cause flow from the sink 11 into the reservoir 21.

The user places the nozzle 35 in his or her mouth and uses switch 40 to turn the pump 31 on or off. This will, of course, cause a jet of water to be emitted out the end of nozzle 35 as it well known in this art. If it is desired to add a medication or other treatment to the water, typically the flow through faucet 16 would be stopped when the reservoir 20 is full, a measured amount of the medication would be added to the water in reservoir 21 and the solution of water and medication would be used until it is gone. If another reservoir 21 full of such water/medication was then desired, the procedure could be repeated.

After the oral hygiene device shown in FIG. 1 has been used sufficiently by the user, it would be time to rinse off the container 20 and place it wherever it is to be stored, for example in the manner shown in FIG. 2-*a* by moving the housing portion 32 of the oral hygiene apparatus in the direction of the arrows in FIG. 2-*a* until it comes to rest in the slots 22 in the position shown in FIG. 2-*b*.

Obviously many modifications and variations of the present invention are possible in light of the above teachings. It is therefore to be understood that, within the scope of the appended claims the invention may be practiced otherwise than as specifically described.

The invention claimed is:

1. An oral hygiene apparatus for use with a water faucet providing a flow of water, the apparatus comprising:
    said oral hygiene apparatus having a pump with an inlet port and an outlet nozzle;
    a sink having a drain disposed therein for permitting water to exit therefrom;
    said water faucet having a source of hot and cold water attached thereto and a faucet outlet disposed at least at times above the drain;
    a reservoir being disposed on the sink above the drain and below the outlet of the faucet, at least portion of the top of the reservoir being open to atmosphere so that water from the faucet outlet can flow downwardly by gravity into the reservoir, said reservoir having a reservoir outlet therein; wherein the reservoir has a top periphery and a pair of depressions in the top periphery for permitting water to overflow to the sink;
    said reservoir having a base for abutment with the sink;
    an opening in the base of the reservoir to permit water to pass from the sink to the drain; and
    a conduit operatively attached to the reservoir outlet and to the inlet port of the pump for permitting water from the reservoir to be pumped to the outlet nozzle.

2. The oral hygiene apparatus of claim 1 wherein a one way check valve is operatively disposed between the reservoir outlet and the inlet port of the pump for allowing water to be pumped from the reservoir to the pump inlet port but preventing a reverse flow of water from the pump to flow back to the reservoir through the conduit.

3. The oral hygiene apparatus of claim 2 wherein the one way check valve is located closer to the reservoir than to the pump inlet.

4. The oral hygiene apparatus of claim 1 wherein medication is disposed in a liquid in the reservoir.

5. The oral hygiene apparatus of claim 1 wherein the oral hygiene apparatus includes a housing to permit a user to hold the housing in one hand and wherein the housing is disposed in the pair of depressions when the oral hygiene apparatus is not is use to permit a more compact storage configuration of the oral hygiene apparatus.

6. The oral hygiene apparatus of claim 1 wherein the sink has a drain with a stopper therein, said stopper having an upper open position and a lower closed position, the base being high enough as to not touch the drain when the drain is in the upper open position thereof.

7. An oral hygiene apparatus said oral hygiene apparatus having a pump with an inlet port and an outlet nozzle for use with a water faucet having a source of hot and cold water attached thereto and a faucet outlet disposed above a drain providing a flow of water, and a sink having a drain disposed therein for permitting water to exit therefrom, the apparatus comprising:

a reservoir being disposed on the sink above the drain and below the outlet of the faucet, at least portion of the top of the reservoir being open to atmosphere so that water from the faucet outlet can flow downwardly by gravity into the reservoir, said reservoir having a reservoir outlet therein; wherein the reservoir has a top periphery and a pair of depressions in the top periphery for permitting water to overflow to the sink;

said reservoir having a base for abutment with the sink;

an opening in the base of the reservoir to permit water to pass from the sink to the drain; and a conduit operatively attached to the reservoir outlet and to the inlet port of the pump for permitting water from the reservoir to be pumped to the outlet nozzle.

8. The oral hygiene apparatus of claim 7 wherein a one way check valve is operatively disposed between the reservoir outlet and the inlet port of the pump for allowing water to be pumped from the reservoir to the pump inlet port but preventing a reverse flow of water from the pump to flow back to the reservoir through the conduit.

9. The oral hygiene apparatus of claim 8 wherein the one way check valve is located closer to the reservoir than to the pump inlet.

10. The oral hygiene apparatus of claim 7 wherein medication is disposed in a liquid in the reservoir.

11. The oral hygiene apparatus of claim 7 wherein the oral hygiene apparatus includes a housing to permit a user to hold the housing in one hand and wherein the housing is disposed in the pair of depressions when the oral hygiene apparatus is not is use to permit a more compact storage configuration of the oral hygiene apparatus.

12. A method of using an oral hygiene apparatus said oral hygiene apparatus having a pump with an inlet port and an outlet nozzle for use with a water faucet having a source of hot and cold water attached thereto and a faucet outlet disposed above a drain providing a flow of water, and a sink having a drain disposed therein for permitting water to exit therefrom, said method comprising:

providing the oral hygiene apparatus of claim 7;

placing a reservoir on the sink above the drain and below the faucet outlet, turning on the water to the faucet;

adjusting a temperature of the water coming from the faucet outlet until the water temperature is at a desired temperature;

using the pump to pump water from the reservoir to the nozzle.

13. The method of claim 12 wherein medication is added to the water in the reservoir.

14. The method of claim 12 including placing the outlet nozzle in a person's mouth and directing flow of fluid therefrom towards the gums and/or teeth of such person for oral hygiene purposes.

15. The method of claim 12 including opening a stopper in the drain so that excess water flowing out of the reservoir can exit out the drain.

\* \* \* \* \*